United States Patent [19]

Barendse

[11] Patent Number: 4,922,016

[45] Date of Patent: May 1, 1990

[54] PROCESS FOR THE PREPARATION OF N-(SULFONYLMETHYL) FORMAMIDE COMPOUNDS

[75] Inventor: Nicolaas C. M. E. Barendse, Den Hoorn, Netherlands

[73] Assignee: Gist-Brocades N.V., Delft, Netherlands

[21] Appl. No.: 385,583

[22] Filed: Jul. 26, 1989

Related U.S. Application Data

[63] Continuation of Ser. No. 29,746, Mar. 24, 1987, abandoned.

[30] Foreign Application Priority Data

Apr. 16, 1986 [EP] European Pat. Off. ........ 86200653.3

[51] Int. Cl.$^5$ ............................................ C07C 103/44
[52] U.S. Cl. ..................................... 564/219; 564/215; 564/222; 558/302; 558/311; 558/312
[58] Field of Search ....................... 564/215, 219, 222; 558/302, 311, 312

[56] References Cited

PUBLICATIONS

Johnson et al, *Organic Syntheses*, 57, 1977, pp. 102–106.

*Primary Examiner*—Mary C. Lee
*Assistant Examiner*—Zinna Northington-Davis
*Attorney, Agent, or Firm*—Bierman & Muserlian

[57] ABSTRACT

N-(sulfonylmethyl)formamides are obtained by reacting a sulfinic acid, formaldehyde and formamide in the presence of a second acid and a controlled amount of water. The formamides can be converted to the corresponding sulfonylmethylisocyanides.

9 Claims, No Drawings

PROCESS FOR THE PREPARATION OF N-(SULFONYLMETHYL) FORMAMIDE COMPOUNDS

PRIOR APPLICATION

This application is a continuation of U.S. patent application Ser. No. 29,746 filed Mar. 24, 1987, now abandoned.

The invention relates to a process for the preparation of N-(sulfonylmethyl)formamides by reacting a sulfinic acid, formaldehyde and formamide in the presence of water and a second acid.

The resulting compounds are important starting materials for the preparation of sulfonylmethylisocyanides, a class of compounds which in recent years have found wide use as "building blocks" in preparative organic chemistry. See for example the survey in Lect. Heterocycl. Chem. 5, S111-S122 (1980). The most frequently used compound of this class is p-toluenesulfonylmethylisocyanide, also known under the short name TosMIC.

Descriptions of possible syntheses of sulfonylmethylisocyanides are found in Tetrahedron Letters, 2367-2368 (1972).

The large scale use of sulfonylmethylisocyanides is, however, seriously hampered because the starting compounds, the N-(sulfonylmethyl)formamides, can not be easily prepared on industrial scale in good yield.

For large scale manufacture of sulfonylmethylisocyanides, a Mannich condensation is preferably used in which a sulfinic acid, formamide and formaldehyde are reacted in the presence of water and formic acid. The N-(sulfonylmethyl)formamide obtained is subsequently dehydrated to the desired sulfonylmethylisocyanide. Full details are to be found e.g. in Organic Syntheses 57, 102-106 (1977), see particularly the Discussion (part 3).

The reactions may be represented by the following reaction scheme:

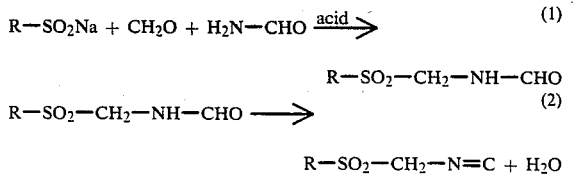

R is an organic group and more specifically R may be a hydrocarbyl or heteroaryl group which may be substituted or unsubstituted. The hydrocarbyl group can be aliphatic, cycloaliphatic, mononucleararyl or polynucleararyl. Aliphatic groups may be alkyl, alkenyl or alkynyl groups. Cycloaliphatic groups may be cycloalkyl or cycloalkylalkyl. Aryl groups may be phenyl or naphtyl. The heteroaryl groups may be groups containing one or more 5,6 or 7-membered rings containing one or more ring nitrogen, oxygen or sulfur atoms. Where substituents are present, one or more substituents may be present and may be selected from alkyl, alkenyl, alkynyl, alkoxy, halogen such as chlorine or bromine, amino, nitro etc. The aliphatic and cycloaliphatic groups may contain up to 10 and preferably up to 6 carbon atoms, alkyl groups most preferably containing 1 to 4 carbon atoms.

Preferably R is an optionally substituted phenyl, or a naphtyl group or a lower alkyl group and more preferably R is the p-methylphenyl group.

The dehydration step (2) proceeds smoothly. Under mild conditions, with easily available and cheap chemicals, a yield of 80-90% can be obtained.

The preceding Mannich condensation (1), however, proceeds with low yields. In Rec. Trav. Chim. Pays Bas 91, 209-212 (1972) five N-(sulfonylmethyl)formamides are reported which have been obtained in yields which range from 15-55%. In Org. Synth. 57, 102-106 (1977) a yield of only 42-47% is mentioned for the production of N-(p-tolylsulfonylmethyl)formamide, the starting compound of TosMIC.

In accordance with the present invention, it has been found that the yield of the Mannich condensation leading to N-(sulfonylmethyl)formamides can substantially be improved, when the reaction is carried out in a reaction medium in which water is absent or is present in only small amounts, not exceeding 40% (w/w), preferably less than 15% (w/w) and more preferably less than 5%. (w/w). By controlling the water content in this way and using an amount which is much less than the amount used in the Organic Syntheses method mentioned before, yields of more than 90% are obtainable. A further advantage of the method according to the invention is that the crude reaction product can be used without further isolation in a subsequent dehydration step to give the corresponding sulfonylmethylisocyanide, so that this last mentioned class of compound can now be manufactured in a more economical one-pot-process.

The sulfinic acid is usually added to the reaction mixture in the form of a salt, for example its sodium salt, from which the sulfinic acid is liberated in situ by the excess acid in the mixture. The preferred acid for this excess is formic acid.

Formaldehyde is added to the reaction mixture as such or in a form from which it is generated in situ for example as paraformaldehyde.

The reactants and the acid are preferably used in excess with respect to sulfinic acid. Optimum yields are obtained with a molar ratio of about 6:1 for formamide, about 5:1 for formaldehyde and about 4:1 for the second acid. Diluents not interfering with the reaction may be used if desired, but it is not usually necessary.

The reaction temperature is usually in the range from about 50° C. to the boiling point of the mixture and preferably is between 85° and 95° C. The best temperature is about 90° C.

The following Examples are given to illustrate the invention. The % yield is calculated on the basis of sulfinate reactant.

EXAMPLE 1

N-(tosylmethyl)formamide

A mixture of 51.22 g (0.2 mol) of sodium p-tolylsulfinate containing about 4 mol $H_2O$, 24 g (0.8 mol) of paraformaldehyde, 60 ml (1.5 mol) of formamide and 38 ml (1 mol) of formic acid was heated up to 90° C. over a 15 min. period in a vessel. The mixture contained about 7% of water. After 2 hours of stirring at this temperature, the clear solution was cooled to 20° C. After seeding and the addition of 400 ml of water, N-(tosylmethyl)formamide crystallized. The crystal suspension was stirred at 19° C. for 30 min. The precipitate was filtered, washed three times with 75 ml of water and dried at 70° C. in vacuo yielding 30.16 g of N-(tosylmethyl)formamide (70.8%). Melting point 109°–111° C.

A considerable extra amount of N-(tosylmethyl)formamide was obtained by extracting the filtrate five times with 100 ml of methylene chloride. The 10.5 g of residue obtained from the combined and evaporated extracts were dissolved in 50 ml of acetone. To this solution 75 ml of water were added. The acetone was evaporated in vacuo. After seeding N-(tosylmethyl)formamide crystallized. This crystalline product was filtered, washed and dried, yielding 8.18 g (19.2%). Melting point 103°–107° C.

The residue of the mother liquor (1.90 g) was dissolved in methylene chloride and the solution passed through a silicagel column. The loaded column was first eluted with toluene to remove all methylene chloride. Subsequently 0.6 l of toluene containing 5% (v/v) acetone were used for elution and finally toluene containing 10% (v/v) acetone was used. The residue from the combined fractions of eluate was dissolved in acetone. Water was added and the acetone evaporated in vacuo. After seeding N-(tosylmethyl)formamide crystallized to give a further 0.49 g (1.15%). Melting point 107.5°–108° C. The overall yield of N-(tosylmethyl)formamide recovered was 38.8 g representing 91% yield based on the sulfinate.

EXAMPLE 2

N-(tosylmethyl)formamide

A mixture of 7.34 g (40 mmol) of 97% dry sodium p-tolylsulfinate, 4.80 g (160 mmol) of paraformaldehyde, 12 ml (13.56 g, 300 mmol) of formamide and 7.6 ml (9.27 g, 200 mmol) of 99% formic acid was heated to 90° C. All reagents are substantially free of water.

After 2 hours of stirring the mixture was cooled to room temperature and 30 ml of water was added whereupon N-(tosylmethyl)formamide crystallized. The resulting N-(tosylmethyl)formamide was washed with water and dried in vacuo. Yield 7.68 g (90.1%). Melting point 109°–111° C.

EXAMPLE 3

N-(phenylsulfonylmethyl)formamide

The procedure of Example 2 was repeated but using 6.77 g (40 mmol) of 97% dry sodium benzenesulfinate in place of the p-tolylsulfinate. Yield of N-(phenylsulfonylmethyl)-formamide was 6.31 g (79.3%). Melting point 106°–107° C.

EXAMPLE 4

N-(beta-naphtylsulfonylmethyl)formamide

The procedure of Example 2 was repeated but using 4.2 g (20 mmol) of dry sodium beta-naphtylsulfinate in place of the p-tolylsulfinate. The amount of the other reactants was halved compared to Example 2.

The yield of the title compound was 4.63 g (93.0%). Melting point 139°–141° C.

EXAMPLE 5

N-(tosylmethyl)formamide

Eight reaction mixtures were prepared each containing the reactants of example 2. To each mixture an increasing amount of x ml of water was added so that they eventually contained 0, 5, 10, 15, 20, 25, 30 and 35 wt % of water.

The mixtures were reacted and worked up as described in example 2. Only to the first mixture 30 ml of water were added. To the other mixtures (30-x) ml of water were added and the resulting N-(tosylmethyl)formamide recovered. The results obtained were as follows:

| Perc. water: | 0 | 5 | 10 | 15 | 20 | 25 | 30 | 35% |
|---|---|---|---|---|---|---|---|---|
| Yields of the title compound | 7.68 | 7.09 | 7.20 | 6.98 | 6.95 | 6.52 | 6.20 | 5.70 g |
| | 90.1 | 83.2 | 84.5 | 81.9 | 81.6 | 76.5 | 72.8 | 66.9% |

Melting points: 109-111° C.

EXAMPLE 6

Methylsulfonylmethylisocyanide

A mixture of 1.02 g (10 mmol) of sodium methylsulfinate, 1.20 g (40 mmol) of paraformaldehyde, 3.0 ml (75 mmol) of formamide and 1.9 ml (50 mmol) of formic acid and substantially free of water was stirred for 2 hours at 90° C. The volatile reactants were distilled off at a temperature of 90° C. and in vacuo. The residue was ultrasonically vibrated with 10 ml of dry acetonitrile at room temperature during 30 minutes. After adding 20 ml of tetrahydrofuran vibration was continued for 15 minutes. The resulting suspension was cooled to 0° C., 13.0 ml (93 mmol) of diisopropylamine were stirred in and 3.1 ml (33 mmol) of phosphorous oxychloride were added. The reaction mixture was alternating vibrated and stirred for one hour at 0° C. and was subsequently poured out into 100 ml of ice/saturated sodium bicarbonate solution and extracted with methylene chloride. The dried and concentrated extract was diluted with 250 ml of ethyl acetate and treated with neutral alumina. The liquid was concentrated to 20 ml and about 50 ml of 40°–60° C. petroleum ether was slowly added. Crystallisation started and another 50 ml of petroleumether was added. Yield 630 mg of the title compound. From the mother liquor another 30 mg of the title compound was obtained.

Total yield 660 mg (55%, based on starting methylsulfinate). Melting point: 50°-54° C. After recrystallisation: 54.5°-55.0° C.

I claim:

1. Process for the preparation of N-(sulfonylmethyl) formamides having an organic group R substituted on the sulfonyl moiety, comprising the reaction of a sulfinic acid having the group R, formaldehyde and formamide and a second acid R being selected from the group consisting of alkyl of 1 to 6 carbon atoms, phenyl, naphthyl and phenyl and naphthyl substituted with 1 to 3 members of the group consisting of halogen, nitro and alkyl of 1 to 4 carbon atoms, characterized in that the reaction medium contains 0 to 35% (w/w) of water.

2. Process according to claim 1, characterized in that the reaction medium contains less than 15% (w/w) of water.

3. Process according to claim 1, characterized in that the reaction medium contains less than 5% (w/w) of water.

4. Process according to claim 1 characterized in that the second acid is formic acid.

5. Process according to claim 1 characterized in that the reaction temperature is between 85 and 95° C.

6. Process according to claim 1 characterized in that the reactants and the second acid are introduced in the reaction mixture in the following molar ratios with respect to the sulfinic acid: formamide 6:1, formaldehyde 5:1 and second acid 4:1.

7. Process according to claim 1 characterized in that N-(tosylmethyl)formamide is prepared.

8. Process according to claim 1 characterized in that the resulting N-(sulfonylmethyl)-formamide is dehydrated to give the corresponding sulfonylmethylisocyanide.

9. The process of claim 5 wherein the reaction temperature is about 90° C.

* * * * *